(12) United States Patent
Bell

(10) Patent No.: US 6,596,291 B2
(45) Date of Patent: *Jul. 22, 2003

(54) COMPOSITIONS AND METHODS FOR TREATING SURFACES INFECTED WITH ECTOPARASITIC INSECTS

(76) Inventor: Thomas A. Bell, 4217 51st Ave. NE., Seattle, WA (US) 98105

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/106,739

(22) Filed: Jun. 29, 1998

(65) Prior Publication Data

US 2002/0009476 A1 Jan. 24, 2002

Related U.S. Application Data

(63) Continuation-in-part of application No. 08/986,090, filed on Dec. 5, 1997, now abandoned.

(51) Int. Cl.$^7$ ............................................. A01N 25/04
(52) U.S. Cl. ................. 424/407; 424/78.02; 424/78.07; 424/406; 424/77; 424/78.31; 424/485; 514/724
(58) Field of Search ..................... 424/405, 407–409, 424/485, 486, 77, 78.31, 406, 78.02, 78.07; 514/715, 722, 723, 724, 729, 738

(56) References Cited

U.S. PATENT DOCUMENTS

| | | | |
|---|---|---|---|
| 3,058,879 A | 10/1962 | Malz et al. ..................... 167/33 |
| 3,719,763 A | 3/1973 | Cline et al. ................. 424/325 |
| 3,836,569 A | 9/1974 | Wommack, Jr. ............. 260/470 |
| 3,927,069 A | 12/1975 | Adams ........................ 260/470 |
| 3,958,007 A | 5/1976 | Wommack, Jr. ............. 424/300 |
| 4,010,278 A | 3/1977 | Adams ........................ 424/309 |
| 4,018,926 A | 4/1977 | Wommack, Jr. ............. 424/258 |
| 4,038,403 A | 7/1977 | Wright, Jr. ................... 424/269 |
| 4,048,302 A * | 9/1977 | Coleman et al. .............. 424/78 |
| 4,147,800 A | 4/1979 | Singer et al. ................ 424/312 |
| 4,156,017 A | 5/1979 | Krüger et al. ............... 424/330 |
| 4,193,986 A | 3/1980 | Cox .............................. 424/28 |
| 4,279,095 A | 7/1981 | Aasen .......................... 43/139 |
| 4,368,207 A | 1/1983 | Lover et al. ................. 424/343 |
| 4,372,977 A | 2/1983 | Lover et al. ................. 424/342 |
| 4,374,853 A | 2/1983 | Workman ..................... 424/303 |
| 4,439,427 A | 3/1984 | Bernstein ..................... 424/199 |
| 4,447,423 A | 5/1984 | Workman ..................... 424/234 |
| 4,491,576 A | 1/1985 | Lover et al. ................... 424/78 |
| 4,497,831 A | 2/1985 | Lover et al. ................. 514/717 |
| 4,630,329 A | 12/1986 | Shores ........................ 15/368 |
| 4,781,922 A | 11/1988 | Bone ............................ 424/92 |
| 4,808,615 A | 2/1989 | Ott et al. ..................... 514/89 |
| 4,927,813 A | 5/1990 | Bernstein ..................... 514/65 |
| 4,929,628 A | 5/1990 | McArthur et al. .......... 514/364 |
| 4,973,589 A | 11/1990 | Barnett et al. ............... 514/245 |
| 5,021,424 A | 6/1991 | Lawton-Wall ............... 514/276 |
| 5,029,411 A | 7/1991 | Keenan ......................... 43/136 |
| 5,057,527 A | 10/1991 | Alig et al. ................... 514/345 |
| 5,095,648 A | 3/1992 | Keenan ......................... 43/136 |
| 5,112,515 A | 5/1992 | Buxton et al. .............. 252/106 |
| 5,114,977 A | 5/1992 | Karrer et al. ................ 514/720 |
| 5,206,228 A | 4/1993 | Collins ........................ 514/141 |
| 5,229,426 A | 7/1993 | Karrer et al. ................ 514/720 |
| 5,266,324 A | 11/1993 | Stendel et al. ............... 424/411 |
| 5,279,256 A | 1/1994 | Brite ............................. 119/85 |
| 5,288,483 A * | 2/1994 | Cardin et al. .................. 424/70 |
| 5,292,504 A | 3/1994 | Cardin et al. .................. 424/70 |

(List continued on next page.)

FOREIGN PATENT DOCUMENTS

| | | |
|---|---|---|
| EP | 0255803 | 2/1988 |
| EP | 0443733 | 8/1991 |
| EP | 0470467 | 4/1992 |
| EP | 0787014 | 8/1997 |
| FR | 2 696 902 A1 | 4/1994 |
| GB | 2 024 626 A | 1/1980 |
| GB | 1 604 622 | 12/1981 |
| GB | 2222949 | * 3/1990 |
| JP | 05 331033 | 12/1993 |
| JP | 06 248291 | 9/1994 |
| WO | WO9116818 | 11/1991 |
| WO | WO 95/35093 | 12/1995 |
| WO | WO9611706 | 4/1996 |
| WO | WO9740058 | 10/1997 |
| WO | WO9805294 | 2/1998 |

OTHER PUBLICATIONS

Elar et al GB08919017 Mar. 28, 1990.*
Elgar et al GB2222949 Mar. 28, 1990.*
Kiergn A4536453 May 10, 1984.*
Kieran A4529748 Jun. 16, 1983.*
Issa et al., "Controlled Release Of Herbicides Bound To Poly[Oligo(Oxyethylene)Methacrylate] Hydrogels," *Journal of Controlled Release 13*: 1–10, 1990.

Primary Examiner—Neil S. Levy
(74) Attorney, Agent, or Firm—Seed I.P. Law Group PLLC

(57) ABSTRACT

Compositions and methods are disclosed for treating a hair-bearing surface of a warm-blooded animal, including humans, dogs and cats infested with an ectoparasitic insect, such as lice and/or fleas. Compositions and methods are also disclosed for preventing the infestation or re-infestation of an ectoparasitic insect, such as lice and/or fleas on a hair-bearing surface of a warm-blooded animal, including humans, dogs and cats. The compositions include either a water-soluble polyalkylene glycol or a water-soluble polyalkylene oxide mixed with a polymer or copolymer comprising polyalkylene oxide having carboxylic acid-containing residues. Methods of the invention include topical application to a hair-bearing surface of an effective amount of a composition of this invention, and maintaining the same on the surface for a sufficient period of time to treat the surface. Further optional steps include washing or rinsing the composition from the surface, as well as combing the hair associated with the treated surface.

12 Claims, No Drawings

U.S. PATENT DOCUMENTS

| | | | |
|---|---|---|---|
| 5,342,611 A | * | 8/1994 | Komori et al. ................ 424/70 |
| 5,362,494 A | * | 11/1994 | Zysman et al. ............. 424/401 |
| 5,416,102 A | | 5/1995 | Barnett et al. .............. 514/351 |
| 5,416,116 A | | 5/1995 | Caupin et al. .............. 514/560 |
| 5,439,924 A | | 8/1995 | Miller ......................... 514/345 |
| 5,441,980 A | | 8/1995 | Fabre et al. ................. 514/531 |
| 5,449,517 A | | 9/1995 | Fitzjarrell ................... 424/195 |
| 5,538,945 A | | 7/1996 | Pallengerg et al. ............ 514/6 |
| 5,547,665 A | | 8/1996 | Upton ..................... 424/94.61 |
| 5,632,999 A | | 5/1997 | Miller ......................... 424/411 |
| 5,712,143 A | | 1/1998 | Grieve et al. ................ 435/212 |
| 5,720,967 A | * | 2/1998 | Hall-Hibbitts et al. ...... 424/405 |
| 5,858,383 A | * | 1/1999 | Precopio ..................... 424/405 |

* cited by examiner

COMPOSITIONS AND METHODS FOR TREATING SURFACES INFECTED WITH ECTOPARASITIC INSECTS

CROSS-REFERENCE TO RELATED APPLICATION

This application is a continuation-in-part of U.S. application Ser. No. 08/986,090, entitled COMPOSITIONS AND METHODS FOR DELOUSING, filed Dec. 5, 1997 now abn.

TECHNICAL FIELD

This invention relates generally to compositions and methods for topically treating a hair-bearing surface of a warm-blooded animal infested with an ectoparasitic insect.

BACKGROUND OF THE INVENTION

Lice and fleas (collectively referred to herein as "ectoparasites") infest a wide range of warm-blooded animals, including humans. A louse is a small, flat-bodied, wingless, biting or sucking insect present as an external parasite on hair-bearing surfaces of various animals. The human lice genera include pubic lice (*Pthirus pubis*, or *Phthirus pubis*), body lice (*Pediculus humanus* var. *corporis*), and head lice (*Pediculus humanus* var. *capitis*).

Pubic lice generally are confined to the hairs of the genital region, while body lice may be found on the hair of the axilla, eyebrows, eyelashes, beards, and hairy body surfaces. Both pubic lice and body lice may be acquired from direct contact with another infested person, from wearing contaminated clothing, from contaminated toilet seats and from contaminated bed linen. Body lice typically occur as the result of crowding in unhygienic conditions, while pubic lice are transmitted sexually.

Head lice are small hard-shelled ectoparasites that cling to hairs of the scalp while feeding, mating and laying eggs. The adult female head louse has a lifespan of about one month, and is ready to mate and reproduce within about a week after hatching. Under ideal conditions, a female head louse may produce up to 100 eggs in her lifetime, most commonly on the hair above the ears and the back of the head of human beings, and near the base of hair shafts. The eggs are cemented to the hair with a tenacious proteinaceous substance. Head lice eggs (commonly referred to as "nits") are protected by a chitinous sheath which surrounds the eggs and are attached to the hair. These eggs hatch in about seven to nine days and become mature in another week. As with pubic and body lice, head lice are also transmitted by personal contact, as well as by common use of brushes, combs or headgear. Poor hygienic and grooming habits are known to contribute significantly to the spread of head lice. Thus, head lice infestations are most serious in areas where the inhabitants have both substandard hygienic facilities and practices.

Lice have plagued mankind for many centuries, and lice infestation can be found throughout documented history. For example, lice have been responsible for the spread of typhus, causing decimation of many armies and navies from the 15th through the 18th centuries. Even today, lice are still considered as disease vectors and present serious health problems throughout the world. In particular, lice are vectors for staphylococcal skin infections, such as impetigo and furunculosis, and are also the principle method of transmission for typhus, trench fever and relapsing fever.

Head lice, pubic lice and body lice are all capable of infesting humans (referred to as pediculosis), the characteristics of which differ markedly within the species. Head lice infestation is characterized by itching and dermatitis. In long standing or neglected cases, scratching may result in marked inflammation, secondary infection by bacteria may occur, resulting in the formation of pustules, crusts and suppuration, and the hair may become matted and give rise to a disgusting odor. Today, head lice is an epidemic in roughly 2–3% of grade school children in the United States and England. Body lice infestation is characterized by intense itching and, in cases of heavy infestation, by red skin eruptions, mild fever, tiredness, irritability and possibly weakness. Pubic lice infestation is characterized by itching, especially in the genital or crural regions.

In addition to spreading diseases, lice carry a wide variety of bacteria on their exterior surfaces, and their fecal matter transmits disease when it enters the puncture wounds inflicted during feeding. As the lice feed on human skin, they inject their digestive juices into the skin. These materials, as well as the puncture wound itself, cause pruritus, which is painful to the animal host. Therapy that simply kills the louse leaves subcutaneous or intradermal residues that continue to itch for a significant time after the infestation is extinguished. Furthermore, scratching during and after the episode frequently leads to painful excoriation.

Previous methods for treating animals infested with lice have not been entirely satisfactory. In the past, chemical agents, including toxic pesticides or insecticides (termed pediculicides) have been used. Unfortunately, these compounds include potent neurotoxins, as well as carcinogens such as DDT, carbaryl, piperonyl butoxide, the synthetic pyrethrin analog permethrin or cholinesterase inhibitors such as neostigmine or prostigmine. Such pediculicides range from mildly toxic (pyrethrins) to toxic (lindane and malathion). All current methods involve the exposure of the scalp and hair to these agents in shampoos or creams, which are then washed off relatively quickly. Because of increased concern about the overall safety of such chemical agents, the search for new and effective pediculicides has intensified.

In addition to safety concerns regarding the current pediculicides, other problems also exist. One drawback is that chemical agents may not achieve the desired efficacy. For instance, lice have developed a significant degree of resistance to all of the topical pesticides. Natural pyrethrins and synthetic pyrethroids are routinely chosen for use in the treatment of warm-blooded animals infested with lice. Natural pyrethrins have their limitations as poor environmental stability, which is a severe drawback in the treatment of lice. Additionally, natural pyrethrins have low residual action due to this instability. The practical effect is that the use of natural pyrethrins necessitates frequent follow-up treatments. Synthetic pyrethroids are cheaper, more available and more stable than natural pyrethrins, and generally more effective against lice than natural pediculicides.

Not only are current treatments generally losing their ability to kill the adult lice and eggs, the dead nits remain firmly attached to the hairs after treatment. This is unsettling to the patient, as well a significant cosmetic problem. The only current means of removing dead nits is with a fine toothed comb, fingers or forceps. These methods are time consuming and less than certain. Furthermore, if the patient is a child, the child must be nit-free to return to school.

Other forms of treatment are physical in nature and include removal of the hair-infested areas in question, followed by washing with strong soap and optionally one of the pediculicides listed above. Clothing or instruments in contact with the affected body parts should also be decontaminated. These forms of treatment, however, are less than satisfactory.

In addition to lice, fleas constitute another ectoparasite that infests a wide range of animals. More specifically, the flea is an insect of the order Siphonaptera, marked by lateral compression, sucking mouth parts, extraordinary jumping powers, and ectoparasitic adult life in the hair and feathers of warm-blooded animals, including birds and mammals. The flea genera include the human flea (*pulex irritans*), the cat flea (*ctenocephalides felis*) and the dog flea (*ctenocephalides canis*). Using a suctorial proboscis on its head and armed with piercing mandibles, the flea inflicts an irritating and often painful bite to obtain the blood upon which it feeds.

In the case of dogs and cats, for example, male and female fleas mate while still in the animal's coat. When the female flea lays her eggs, the eggs do not adhere to the fur, but fall off and are distributed to the animal's environment. By this mechanism, the total environment of the animal is infested with flea eggs and infestation is greatest in locations where the animal spends most of its time.

Fleas require a blood meal in order to become sexually mature. Once sexually mature, the fleas are able to reproduce. After their first blood meal, fleas undergo a shift in metabolism such that they cannot survive for any time off the host. The blood must come from the correct host and the female flea's appetite requires that she consume as much as 5 times her body weight of blood each day.

Flea eggs hatch to larvae in about two days There are three larval stages, each lasting about three days. In the last stage, the larva spins a cocoon and transforms into a pupa. Under optimum conditions (e.g., 33° C. and 65% relative humidity), eggs develop through larvae to pupae in about 8–10 days. After a further period of approximately 8 days, the pupae develop into young adult fleas in the cocoon, still dispersed in the pet's environment.

The young adult fleas wait until they sense the presence of an acceptable host animal, emerge from their cocoon and attempt to jump onto the host. The pre-emerged adult fleas sense, by carbon dioxide tension and/or vibrations, the presence of an animal host, and then emerge explosively and jump into the air and onto the passing host.

Under suitable environmental conditions of temperature and humidity, unfed fleas that fail to find a host can survive for some time in the environment, waiting for a suitable host. It takes at least three weeks for eggs to develop to pre-emerged adults, at which time the fleas are able to reinfest a host animal. However, the pre-emerged adults can remain viable in the cocoon for months, and as long as one year. In addition, under sub-optimal temperature conditions, it can take 4–5 months for eggs to develop into pupae containing pre-emerged adults.

As with lice, mankind has been waging a war against fleas for a very long time. In fact, fleas have been found embalmed along with King Tut's cat. Flea infestation of animals is a health problem and economic concern because fleas are known to cause and/or transmit a variety of diseases. In addition to various diseases, bacteria are also carried by the flea and transmitted in the course of the bite. Fleas cause and/or carry infectious agents that cause, for example, flea allergy dermatitis, anemia, murine typhus, plague and tapeworm.

In addition to the transmittance of disease, infestation of dogs and cats with fleas has several undesirable effects for the animals. Such undesirable effects include local irritation and annoying itching which leads to scratching. Such scratching may even be to the point that open wounds or sores result, leading to secondary bacterial infections. In addition, a high proportion of pet animals, particularly dogs, become allergic to flea saliva, resulting in the chronic condition known as flea bite allergy (or flea allergy). This condition causes the animal to bite and scratch, leading to excoriation of the skin, secondary pyrogenic infection, hair loss, and chronic severe inflammatory skin changes. Allergic pets may suffer severe skin reactions to the bite of even a few fleas. These infested animals create a nervous impression and become more and more unattractive and irritable. Furthermore, most dogs and cats that are infested with fleas also become infected with *Dipylidium caninum*, the tapeworm transmitted by fleas.

Newly emerged fleas may attack any mammal, including humans, although they are not capable of full reproductive potential if human blood is their sole source of nutrition. Thus, the human owner of an infested dog or cat may be bitten by fleas. Some humans may suffer allergic skin disease as a result of such bites and/or from their excreta. It has, therefore, been desirable to find an effective method of controlling fleas that infest dogs and cats.

The medical and veterinary importance of flea infestation has prompted the development of reagents capable of controlling flea infestation. Early remedies included fumigation, and sulfur was used as early as 1,000 B.C. as a fumigant. Marco Polo used a sulfur-based oil as a mange treatment in 1300 A.D. Currently, a number of methods for the control of fleas are known, but all have various drawbacks.

Commonly encountered methods to control flea infestation are generally focused on use of insecticides in formulations such as sprays, shampoos, dusts, dips, or foams, or in pet collars. A large number of insecticidal active compounds have been disclosed for combating fleas, typical of these chemicals are propoxur, d-Limonene, cyano(3-pheoxypheny)methyl 4-chroroalpha (i-methylethyl) beneneacetate, pyrethrin, piperonyl butoxide and N-octyl bicycloheptane dicarboximide. Insect development inhibitors, such as fipronil, methoprene, or cyromazine, can also be added.

Unfortunately, many of the above insecticides and development inhibitors are often not successful in completely reducing flea populations on the pet. Like most insects, fleas can adapt to survive exposure to normal toxic agents. Additionally, the tolerance of dogs and cats to chemical agents varies Thus, if an insecticidal agent is employed, it is desirable to have a multiplicity of agents and methods available for controlling fleas.

A second problem associated with the use of insecticidal agents to control fleas is that many of the agents have been banned from most countries because of environmental persistence of residues and their effect on certain wildlife. Many of these chemicals are not rapidly biodegradable and constitute an environmental hazard if misused.

Aside from the environmental risks, many of the effective toxic agents have been banned because of long-term health risks, including risks of cancer to the pets and chronically exposed humans. In the United States, even some currently approved and available toxic agents that are effective against fleas are under scrutiny because of concerns for long-term health hazards to pets and to their owners. Additionally, many of these chemicals cannot be applied to the fur of animals, such as cats, that self-groom by licking the skin and fur. Even persons applying these flea killing chemicals to animals must often be very careful to avoid excessive contact with them. Those grooming animals must often wear rubber gloves to avoid continuous contact with the chemicals, must exercise care in keeping the chemicals out of the eyes and away from the mucus membranes, and avoid breathing vapor from the chemicals over long periods.

Flea removal vacuum systems have also been tried, such as the system disclosed in U.S. Pat. No. 4,279,095 which employs the use of a rather coarse brush of flexible, hollow rubber or plastic tubes to agitate the pet's coat and draw the disturbed fleas and eggs by vacuum through a plenum chamber to a trapping filter. However, application of sufficient vacuum, by itself, to remove a meaningful percentage of the flea population hiding in, and clinging to, the coat of a particular pet has proven difficult in practice because the vacuum effect of a household vacuum cleaner alone does not effectively collect a significant percentage of the live fleas on a pet.

Another approach is flea combs. However, they require the pet owner to comb the animal intensively and frequently. Depending on the size of the animal, this may take from several minutes to an hour. Not every animal will always patiently put up with being combed, nor is every owner prepared to sacrifice time for this operation. Like the vacuum system, the comb alone does not effectively remove a significant percentage of the live fleas on a pet.

The use of anti-flea shampoos in many cases is impossible since most cats and a large number of dogs simply refuse to be given a bath. Furthermore, the effect of such bathing does not last for more than about a week and the laborious procedure then must be repeated Similar problems are encountered when using dips or rinses. Even the use of dusting powders is not tolerated by many animals without resistance since it takes several minutes to treat the entire surface of the coat uniformly and some dust is bound to get into the mouth, nose, and eyes of the animal. Even in the case of careful application, it is impossible to prevent the powder from being inhaled by the animal or its owner, and there is virtually no way for the owner to avoid an intensive contact with the active ingredient.

Several anti-flea organophosphorus compounds are available in the form of spot-on formulations. These are applied to a limited spot on the coat. In general, they exhibit good short-term activity against adult fleas, but when applied often the compositions have problematic toxicity. Some organophosphorus compounds are administered orally but have narrow safety limits and must never be applied simultaneously with other organophosphorus compounds.

More recently, the use of pet collars, in which an insecticide gas generating composition is included, have been widely adopted. Flea collars are very effective temporarily. A particular weakness of this method of treatment, however, is that it is normally effective in a very limited region of the animal's body. In general, 100% kill is achieved in the region of the neck and thorax; however, more remote parts of the body are hardly affected. Medallions are also available which can be attached to the collar. However, their effectiveness is also unsatisfactory since they do not come into sufficient contact with the animal's coat.

The collar and medallion also suffer from certain disadvantages. For instance, pet collars containing the insecticide dimethyl, 2,2-dichlorovinyl phosphate, (DDVP), have been widely used for the purpose of controlling fleas on dogs and cats. DDVP has been reported in the literature to have an objectionable depressing effect on the plasma and red cell cholinesterase. This is particularly acute at high concentrations which are produced during the first few days after a collar has been applied to the neck of the animal. Additionally, local skin irritation has occurred at the site of the collar especially when the collar is first placed on the animal.

Further, many of the known techniques disclosed above are principally directed to the control of adult fleas in the coat of the host animal, and do not take into account the different juvenile stages of the fleas existing in the animals' coats as well as on or in the floor, carpets, bedding, chairs and other places the infested animal usually comes into contact. The long life cycle, and especially the extended period of pre-emergence dormancy, has made flea control particularly difficult.

Accordingly, while advances have been made in the field of removing ectoparasitic insects, such as lice and fleas, further improvements are still needed. For example, compositions and methods are needed to effectively immobilize such ectoparasites and, in the case of lice, unlock the bond between the lice egg and the hair to ease removal of the eggs. Additionally, treatment is needed to which ectoparasites cannot evolve a resistance. The present invention fulfills these needs and provides further related advantages.

SUMMARY OF THE INVENTION

In brief, the present invention discloses compositions and methods for treating a hair-bearing surface of a warm-blooded animal, including humans, infested with an ectoparasitic insect. Additionally, the present invention discloses compositions and methods for preventing the re-infestation of an ectoparasitic insect on a hair-bearing surface of a warm-blooded animal. This is accomplished by topically applying to a hair-bearing surface of a warm-blooded animal in need of such treatment or prevention, an effective amount of a composition of this invention, and maintaining the composition on the surface for a sufficient period of time to treat the surface or to prevent re-infestation thereof by the ectoparasitic insect. Methods of this invention further include washing or rinsing the treated surface to remove lice or flea eggs, as well as the removal of the same by means of a comb or vacuum. Frequent prophylactic applications followed by combing or vacuuming can prevent infestations, and is especially appropriate in epidemic situations.

Compositions of this invention include, in one embodiment, a water-soluble polyalkylene glycol, such as polyethylene glycol, with a molecular weight ranging from 100,000 to 8,000,000. The compositions of this invention may also include further optional compounds, such as an antioxidant or a pediculicide.

These and other aspects of this invention will become evident upon reference to the following detailed description.

DETAILED DESCRIPTION OF THE INVENTION

As mentioned above, this invention provides methods and compositions for treating a hair-bearing surface of a warm-blooded animal, including humans, infested with an ectoparasitic insect, as well as methods and compositions for preventing re-infestation of an ectoparasitic insect on a hair-bearing surface. More specifically, this invention provides methods for the topical application of an effective amount of a composition to the surface of a warm-blooded animal, for a sufficient period of time to treat the surface and/or prevent the re-infestation thereof As used herein, the following terms have the meanings set forth below:

"Ectoparasitic insect" means any of the numerous, usually small, invertebrae animals of the class Hexapoda, having an adult stage characterized by three pairs of legs, a segmented body and being parasitic on hair-bearing surfaces of the host.

Ectoparasitic insects of the present invention include, but are not limited to, fleas and lice.

"Lice" means any of various small, flat-bodied, wingless, biting or sucking insects of the order Anoplura present as an external parasite on hair-bearing surfaces of various animals. The louse may be either the adult louse or the lice egg (e.g., nit). The human lice genera include pubic lice (*Pthirus pubis*, or *Phthirus pubis*), body lice (*Pediculus Humanus* var. *corporis*), and head lice (*Pediculus humanus* var. *capitis*).

"Flea" means any of the various small, wingless, blood-sucking insects of the order Siphonaptera, that have legs adapted for jumping, and are parasitic on hair-bearing surfaces of warm-blooded animals. The flea may be either the adult flea or the flea egg (e.g., nit). The flea genera include the human flea (*Pulex irritans*), the cat flea (*Ctenocephalides felis*) and the dog flea (*Ctenocephalides canis*).

"Nit" means the egg of an ectoparasitic insect, and includes the eggs of both lice and fleas.

"Treating" means immobilizing and/or removing ectoparasitic insects from the surface. Removal of the immobilized lice or fleas from the treated surface may be accomplished by a subsequent step, which may take a variety of forms as discussed in greater detail below. An important aspect of this invention is that treating facilitates the subsequent removal of the immobilized lice or fleas. With respect to the louse eggs or nits, treating effects the nit cement that holds the eggs to the hair, thus facilitating their subsequent removal.

"Prevention" means to avoid the ectoparasitic infestation on a hair-bearing surface of a warm-blooded animal from occurring, or to hinder or impede, in advance, such infestation.

"Effective amount" means an amount sufficient to attain the desired result. The effective amount may include an amount in excess necessary to attain the desired result.

"Water-soluble" means capable of being dissolved in water without the aid of a detergent or similar agent.

Compositions of this invention contain a water-soluble polyalkylene glycol. In one embodiment, the polyalkylene glycol is polyethylene glycol. Alternatively, compositions of this invention contain a mixture of a water-soluble polyalkylene oxide and a polymer or copolymer of polyalkylene oxide having carboxylic acid-containing residues.

A water-soluble polyalkylene glycol is represented by the formula $HO-(R-O)_n-H$. Thus, the polyalkylene glycol contains two terminal hydroxyl groups (—OH), with a mid-section composed of repeating alkyleneoxide groups (—RO—). The letter "n" in the formula represents the number of repeating alkyleneoxide units. This number may range from about 5 to several thousand. As the number of repeating units increases, the molecular weight of the polyalkylene glycol will also increase. In one embodiment, the molecular weight of the polyalkylene glycol, in terms of number average molecular weight, ranges from about 100,000 to about 8,000,000.

In one embodiment, the polyalkylene glycol constitutes from about 0.01 to about 45 weight percent by weight of the composition (based on the total weight of the composition). Thus, the ratio of the weight of polyalkylene glycol to the weight of the entire composition will be between about 0.01 to 45 percent. The composition may be prepared in a concentrated form, with little or no water. In such a composition, polyalkylene glycol will comprise about 45 weight percent by weight of the composition. Alternately, the composition may be prepared, with water present up to 90 percent by weight of the composition. In such a composition, polyalkylene glycol will comprise about 0.1 to about 1 percent by weight of the composition. Additionally, the composition may be prepared in a diluted form, with water present in an excess of 90 percent by weight of the composition. In such a composition, polyalkylene glycol will comprise about 0.01 to 0.1 percent by weight of the composition.

In one embodiment, the alkylene group, R, of the polyalkylene glycol is $C_1-C_{10}$ alkylene, $C_3-C_9$ alkylenecycloalkyl or $C_7-C_{20}$ alkylenearyl. As used herein, alkylene group includes both straight chained and branched groups and include, but are not limited to, methylene (—CH$_2$—), ethylene (—CH$_2$CH$_2$—), propylene (—CH$_2$CH$_2$CH$_2$—), and pentylene (—CH$_2$(CH$_2$)$_3$CH$_2$—).

A $C_3-C_9$ alkylenecycloalkyl includes both straight chained and branched alkylene groups with the number of carbon atoms independently ranging from three to nine for the alkylene group and from three to nine for the cycloalkyl group. Thus, the number of carbon atoms in the alkylene and the number of carbon atoms in the cycloalkyl may each independently range from three to nine. The cycloalkyl is covalently bonded to the alkylene. As used herein, a cycloalkyl is any cyclic moiety containing carbon and hydrogen, wherein carbon atoms are bonded in a sequential pattern forming a non-aromatic ring system. Representative examples of $C_3-C_9$ alkylenecycloalkyl include, but are not limited to, cyclopentylethylene, 1-cyclohexyl-3-methyl-octylene, and 1-cyclopentyl-3-tert-butyl-heptylene.

A $C_7-C_{20}$ alkylenearyl includes both straight chained and branched alkylene groups with the number of carbon atoms independently ranging from seven to twenty for the alkylene group and from seven to twenty for the aryl group. Thus, the number of carbon atoms in the alkylene and the number of carbon atoms in the aryl may each independently range from three to nine. The aryl is covalently bonded to the alkylene. As used herein, an aryl group is any cyclic aromatic moiety containing carbon and hydrogen wherein carbon atoms are bonded in a sequential pattern forming an aromatic ring system. Representative examples of $C_7-C_{20}$ alkylenearyl include, but are not limited to, benzylethylene, 1-phenylheptylene, 2-phenylpropylene and 2-phenyl-3-methyl-octylene.

In one embodiment of the present invention, the polyalkylene glycol is in the form of a gel. As used herein a gel means a gelatinous, jelly-like colloid in which the dispersed phase has combined with the continuous phase to produce a semisolid material.

In another embodiment of the present invention, the polyalkylene glycol is polyethylene glycol. As used herein, polyethylene glycol is represented by the formula $H-(O-CH_2-CH_2)_n-OH$, where n is greater than or equal to 4.

A polymer or copolymer of polyalkylene oxide having carboxylic acid-containing residues is represented by the formula $R_5O-(R_6(COOH)O)_n-H$. The letter "n" in the formula represents the number of repeating alkylene carboxylic acid units, and may range from about five to several thousand. Thus, the polymer or copolymer contains a terminal alkoxy group ($R_5O$), with a mid-section composed of repeating alkylene oxide groups with carboxylic acid-containing residues ($R_6$(COOH)O), and a terminal hydroxy group (OH). $R_5$ of the alkoxy group is a straight chained or branched $C_1-C_{10}$ alkyl group. The repeating monomer, ($R_6$(COOH)O), can be either acrylic acid or methacrylic acid, wherein $R_6$(COOH) is $CH_2$=CH(COOH) when the monomer is acrylic acid, and wherein $R_6$(COOH) is $CH_2$=C($CH_3$)(COOH) when the monomer is methacrylic acid.

Thus, in another embodiment of this invention, the composition contains polyalkylene oxide and a polymer or copolymer of polyalkylene oxide having carboxylic acid-containing residues. In one embodiment, the combination of polyalkylene oxide and the polymer or copolymer together constitutes from about 0.1 to about 99 percent by weight of the composition, based on the total weight of the composition. Thus, the ratio of the combined weight of polyalkylene oxide and the polymer or copolymer to the weight of the entire composition will be between about 0.1 to 99 percent. The composition may be prepared in a concentrated form, with little or no water. In such a composition, polyalkylene oxide and the polymer or copolymer together will comprise up to about 99 percent by weight of the composition. Alternately, the composition may be prepared with water present in an excess of 90 percent by weight of the composition. In such a composition, polyalkylene oxide and the polymer or copolymer together will comprise up to about 0.15 percent by weight of the composition. Additionally, the composition may be prepared in a diluted form, with water present in excess of 99 percent by weight of the composition. In such a composition, polyalkylene oxide and the polymer or copolymer together will comprise about 0.1 percent by weight of the composition.

In one embodiment, the compositions of this invention further comprise an antioxidant. As used herein, an antioxidant refers to an agent that inhibits or slows down or prevents the deterioration of materials, present in the composition, through oxidative processes. The specific antioxidant employed will depend on the desired composition. In one embodiment, the antioxidant is methylparaben. As used herein, methylparaben is 4-Hydroxybenzoic acid methyl ester.

Alternatively, suitable compositions are commercially available, although not recognized for use in the practice of the present invention. For example, Wallace-O'Farrell Inc. (Puyallup, Wash.) sells a composition under the trademark SLIPPERY STUFF® gel. SLIPPERY STUFF® gel is sold as a glycerin-free, hygienic, water-based, water-soluble, pharmaceutical lubricant. SLIPPERY STUFF® is an aqueous gel comprising polyethylene oxide as the preferred polyalkylene oxide; methylparaben as the antioxidant and sodium carboxypolymethylene as the preferred polymer or copolymer of polyalkylene oxide having carboxylic acid-containing residues resulting from the polymerization of a monomer selected from acrylic acid, methacrylic acid and salts thereof.

The methods of the present invention provide for topically contacting a composition as described above with a hair-bearing surface of a warm-blooded animal. The surface may be infested with lice, infested with nits, infested with fleas, infested with any combination thereof. If the composition is applied to a surface that is infested with lice, the composition may be applied in order to immobilize and remove the lice. If the composition is applied to a surface that is infested with nits, the composition may be applied in order to ease the subsequent removal of nits from the surface, whether dead, immobilized, or alive. If the composition is applied to a surface that is infested with fleas, the composition may be applied in order to immobilize and remove the fleas.

In one embodiment, the surface to which the composition is to be applied is a human body. Ectoparasites are found, on humans, most commonly, where hair is found on the body. Such areas include the scalp and hair on the scalp, the hairs of the genital region, the hair of the axilla, eyebrows, eyelashes, beards, and the body surface. In one embodiment, the surface is the head and hair on the head. In another embodiment, the surface is hair-bearing surface on the body of a human. In a further embodiment, the surface is the genital region of a human.

The treatment methods of the invention are achieved by topically applying a composition as described above. The composition may be topically applied to the surface by, for example, pouring the composition on the surface, or rubbing the composition over the surface When the composition is topically applied as described above, the composition should thoroughly saturate the surface. In order to thoroughly saturate the surface with the composition, a sufficient or adequate amount of composition should be employed.

The composition completely immobilizes lice and fleas within a few seconds after application, and the lice or fleas begin to suffocate. After extended continuous exposure, the lice or fleas would eventually die.

In a further embodiment, the method of this invention comprises the further step of removing the immobilized ectoparasite from the treated surface, including for example, removal of immobilized lice, fleas or nits from the treated surface. This may be accomplished by combing the hair with a fine-toothed, lice removal comb after the composition has been topically applied, thereby lifting the lice, fleas, or nits from the treated hair with the comb. In another embodiment, the surface may be washed or rinsed or washed and rinsed after the composition has been topically applied.

In this context, washing means applying soap, a detergent, a bleaching agent or a surfactant to the surface, preferably in the presence of water or another liquid, by immersing, dipping, rubbing or scrubbing, thereby cleansing the surface. "Rinse" means to pass water or another liquid over the surface thereby cleansing the surface. "Combing" means to dress, arrange, sort, smooth, fasten or organize hair utilizing a comb or any thin, toothed strip of plastic, metal, bone, rubber, or other material. In another embodiment, the surface is vacuumed after the composition has been topically applied. "Vacuuming" means the application of an apparatus on or close to the surface to remove debris from the surface by drawing the debris from the surface to the apparatus with the use of suction or a partial vacuum. Such a vacuuming apparatus may even include a combing device as mentioned supra.

The compositions and methods employed in the present invention overcome all the problems associated with the prior art methods and compositions. The compositions and methods employed in the present invention are non-toxic and environmentally safe. The compositions pose no known health risk to humans, dogs or cats. These compositions and methods are also inexpensive, yet effective (i.e., the ectoparasite cannot develop a resistance to the compositions, the compositions effectively suffocate the ectoparasite and the compositions break the bond between the lice nit and hair shaft). Additionally, dogs and cats who refuse to be given a bath or who do not tolerate being exposed to a dusting powder or spray do not react aggressively to the compositions and methods of the present invention.

The present invention is illustrated by the following examples, which are to be regarded as illustrative rather than restrictive. Unless otherwise noted, all parts and percentages in the examples, as well as the specification and claims, are by weight.

EXAMPLE 1

This example illustrates the preparation of a composition for topically treating a hair-bearing surface of a warm-blooded animal infested with an ectoparasitic insect and/or preventing infestation of the same. The composition is a gel. The formulation is as follows:

| | |
|---|---|
| Deionized Water | 99.37% |
| Methyl Paraben | 0.13% |
| sodium carboxypolymethylene | 0.17% |
| Poly(ethylene)oxide | 0.27% |
| Sodium Hydroxide | 0.06% |

The composition is prepared by dissolving the sodium hydroxide in the deionized water. While stirring, poly(ethylene)oxide, polyacrylic acid, and methyl paraben are sequentially added.

EXAMPLE 2

This example illustrates the method of treating a child's scalp infested with lice.

The child's hair is brushed to remove tangles, and the brush is boiled for 30 seconds before reuse. A sufficient amount of the gel composition is liberally applied to the outer edges of the child's scalp so as to form a barrier that prevents the lice from escaping. A sufficient amount of the gel composition is liberally applied to the rest of the child's scalp such that the entire scalp and hair are completely saturated. If the child has long hair, a shower cap is placed on the child's head for approximately 30 seconds. After applying the gel, the child's hair is parted and sectioned, and a fine-toothed comb is brushed through the sections of the hair for about thirty seconds such that the entire scalp and hair are completely combed.

After each time the comb is passed through the hair, the comb is wiped on a white or other light colored disposable towel, such as a paper towel, so the user can see the lice, nits or fleas combed out of the child's hair. If the child's hair dries before completion, additional gel composition is applied to the child's hair, and the brushing is continued. The child's hair is combed until no lice, nits or fleas are found. The comb is then boiled for approximately 30 seconds or washed and then dried. The disposable towels are burned or placed in a plastic bag and thrown away.

The child's hair is then washed or rinsed thoroughly with warm water and then blown dry. The child's hair and scalp are then inspected for any lice, nits or fleas that may have been missed. If additional lice, nits or fleas are located, the gel composition is re-applied and the child's hair is sectioned and re combed. After each re-application, the hair is combed and the comb is then boiled or washed and dried. The entire procedure is performed twice a day for five days, after which time the lice are effectively immobilized and removed, there by preventing re-infestation.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for treating a hair-bearing surface of a warm-blooded animal infested with an ectoparasitic insect, comprising:

topically applying to the surface an amount of a film-forming composition effective to immobilize the ectoparasitic insect, the composition consisting essentially of:

a water-soluble polyalkylene glycol represented by the formula $HO-(R-O)_n-H$;

wherein R is C1–C10 alkylene, C3–C19 alkylenecycloalkyl or C7–C20 alkylenearyl, and n is a number sufficient to provide a number average molecular weight of at least about 100,000; and a polymer or copolymer of polyalkylene oxide represented by the formula $R_5O-(R_6(COOH)O)_n-H$ wherein $R_5$ and $R_6$ are selected from straight-chained or branched $C_1-C_{10}$ alkylene groups, or $R_5$ is H, and n is a number sufficient to provide a number average molecular weight of at least about 100,000;

maintaining the composition on the hair-bearing surface for a sufficient period of time to immobilize the ectoparasitic insect; and then removing the immobilized ectoparasitic insect from the hair-bearing surface.

2. The method according to claim 1 wherein the polymer or copolymer of polyalkylene oxide is polyacrylic acid, methacrylic acid or salts thereof such that $R_6(COOH)$ is acrylic acid when $R_6$ is $CH_2=CH(COOH)$ and $R_6(COOH)$ is methacrylic acid when $R_6$ is $CH_2=CH(CH_3)(COOH)$.

3. The method according to claim 1 wherein the polymer or copolymer of polyalkylene oxide contains residues resulting from the polymerization of monomers selected from polyacrylic acid and methacrylic acid such that $R_6(COOH)$ is acrylic acid when $R_6$ is $CH_2=CH(COOH)$ and $R_6(COOH)$ is methacrylic acid when $R_6$ is $CH_2=CH(CH_3)(COOH)$.

4. The method according to claim 1 wherein the number of acrylic acid and methacrylic acid residues is greater than the number of acrylate ester and methacrylate ester residues.

5. The method according to claim 1 wherein the polyalkylene oxide having carboxylic acid-containing residues, comprises a plurality of alkylene groups wherein the alkylene groups are independently selected from $C_1-C_{10}$ alkylene, $C_3-C_9$ alkylenecycloalkyl and $C_7-C_{20}$ alkylenearyl.

6. The method according to claim 1 wherein the polyalkylene oxide and the polymer or copolymer together constitute between about 0.1 to 99 weight percent of the entire composition.

7. The method according to claim 1 wherein the polymer or copolymer constitutes between about 0.1 to about 85 weight percent of the composition.

8. The method according to claim 1 wherein the warm-blooded animal is a human.

9. The method according to claim 1 wherein the surface in need of treatment is the scalp of the animal.

10. The method according to claim 1 wherein the surface in need of treatment is the genitalia of the animal.

11. The method of claim 1, further comprising washing or rinsing the surface in need of such treatment.

12. The method of claim 1, further comprising combing or vacuuming the surface in need of such treatment.

* * * * *